United States Patent [19]

Deckelbaum

[11] Patent Number: 4,785,806

[45] Date of Patent: Nov. 22, 1988

[54] LASER ABLATION PROCESS AND APPARATUS

[75] Inventor: Lawrence I. Deckelbaum, Woodbridge, Conn.

[73] Assignee: Yale University, New Haven, Conn.

[21] Appl. No.: 1,376

[22] Filed: Jan. 8, 1987

[51] Int. Cl.$^4$ ............................................. A61N 5/06
[52] U.S. Cl. .............................. 128/303.1; 128/634; 128/666
[58] Field of Search ...................... 128/303.1, 395, 634, 128/653, 665–667; 219/121 L, 121 LA, 121 LB, 121 LM; 604/20

[56] References Cited

U.S. PATENT DOCUMENTS

| | | | |
|---|---|---|---|
| 4,556,057 | 12/1985 | Hiruma et al. | 128/395 |
| 4,641,650 | 2/1987 | Mok | 128/303.1 |
| 4,641,912 | 2/1987 | Goldenberg | 128/303.1 |
| 4,648,892 | 3/1987 | Kittrell | 128/303.1 |
| 4,681,104 | 7/1987 | Edelman | 128/303.1 |
| 4,686,979 | 8/1987 | Gruen et al. | 128/303.1 |

FOREIGN PATENT DOCUMENTS

| | | | |
|---|---|---|---|
| 111060 | 6/1984 | European Pat. Off. | 128/303.1 |
| 8606642 | 11/1986 | PCT Int'l Appl. | 128/303.1 |

OTHER PUBLICATIONS

"Use of Pulsed Energy Delivery . . . " by Deckelbaum et al.; J. Am. Coll. Cardiol., No. 4, 1986, pp. 848–908.
"Reduction of Laser Induced . . . " by Deckelbaum et al.; Am. J. Cardiol., vol. 56, 10/1/85, pp. 662–666.
"For Ultraviolet Laser Ablation of Atherosclerotic Lesions" by Linsker et al., Lasers in Surg. & Med., 4/1984; pp. 201–206.
"Selective Absorption of Ultraviolet Laser Energy . . . " by Murphy-Chutorian Am. J. Cardiol., vol. 5; 5/85; pp. 1293–1297.
"Detection of Aortic Atheromatrosis . . . " by Edholm et al.; J. of Atherosclerosis Res., vol. 5; 1965; pp. 592–595.

Primary Examiner—Lee S. Cohen
Assistant Examiner—David Shay
Attorney, Agent, or Firm—Darby & Darby

[57] ABSTRACT

A process and apparatus for ablating atherosclerotic or tumorous tissues is disclosed. Optical fibers direct low power light energy at a section of tissue to be ablated to cause the section to fluoresce. The fluorescence pattern is analyzed to determine whether the fluorescence frequency spectrum is representative of normal or abnormal tissue. A source of high power ultraviolet laser energy directed through an optical fiber at the section of tissue is fired only when the fluorometric analysis indicates that it is directed at abnormal tissue.

9 Claims, 2 Drawing Sheets

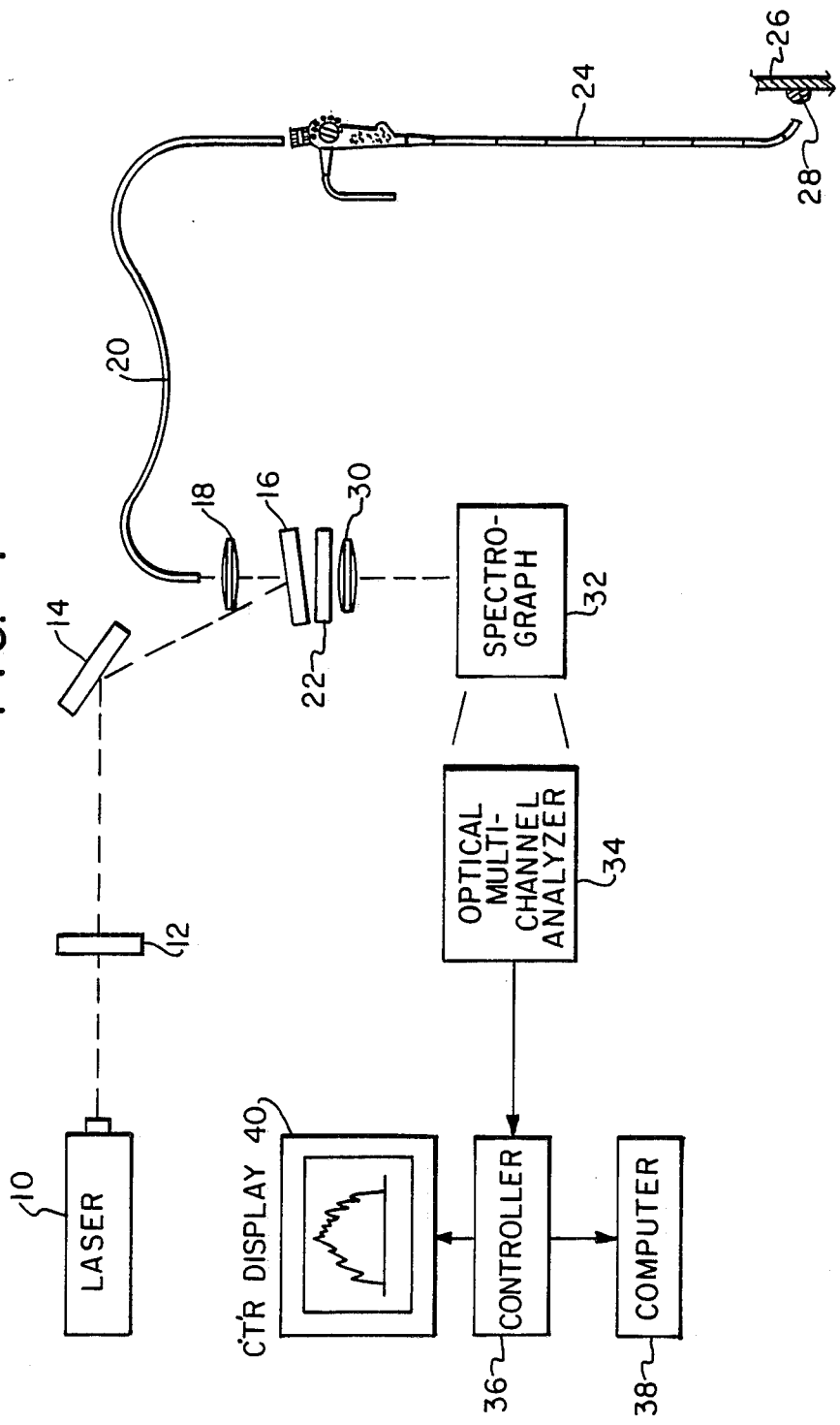

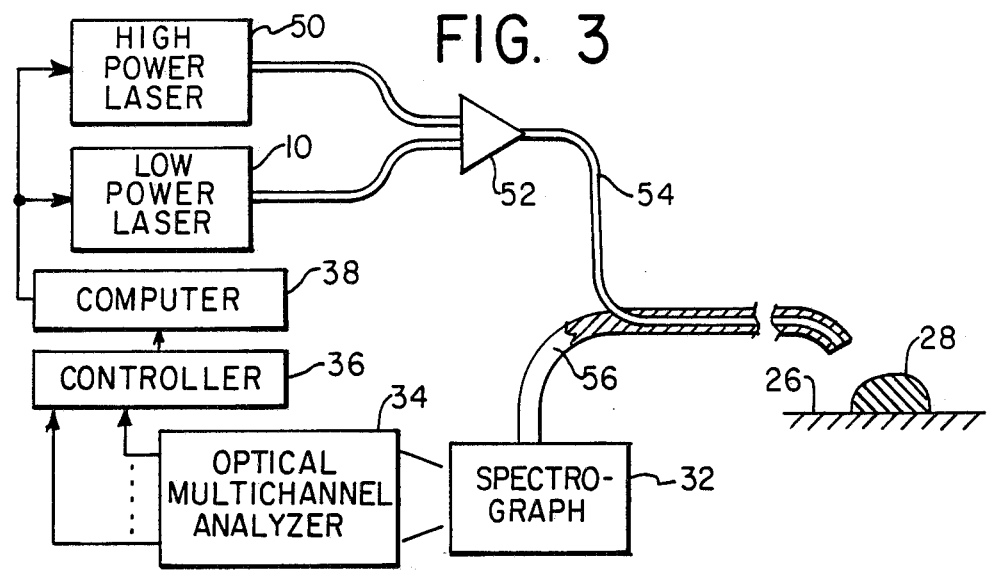
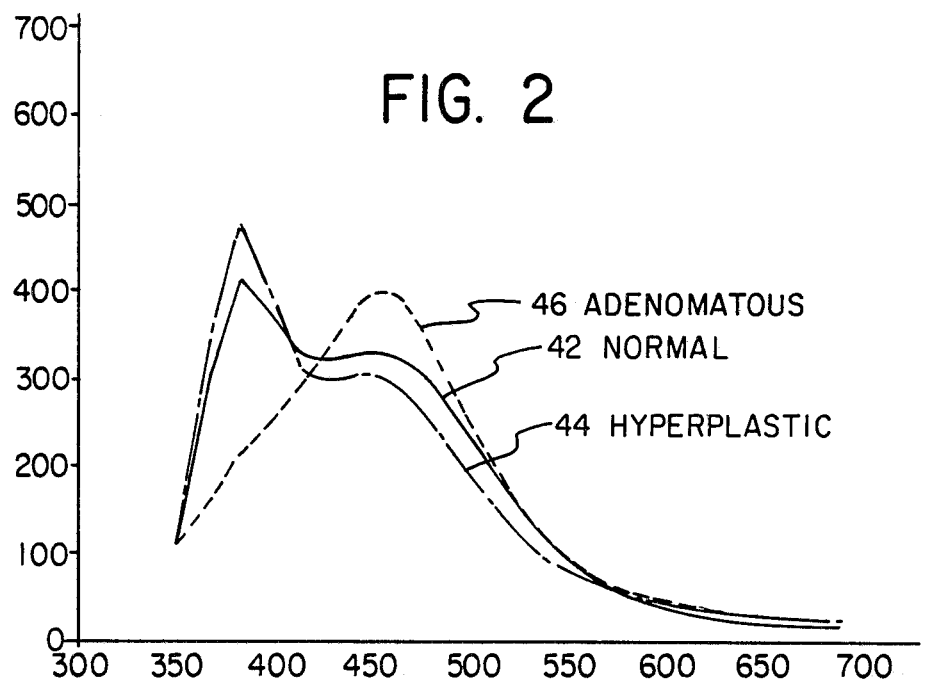

LASER ABLATION PROCESS AND APPARATUS

This invention relates to laser ablation of human tissue.

Lasers have been used to evaporate (ablate) atherosclerotic and cancerous tissue in humans. Particularly when used to ablate arterial atherosclerotic plaque (a process known as laser angioplasty), the use of a laser presents severe hazards because of the possibility that the artery will be perforated by the laser.

Thus, there exists a need in the field of laser angioplasty to provide for control of the laser so that only atherosclerotic plaque is ablated.

It has been recognized that atherosclerotic plaque has a fluorescence pattern which differs from the fluorescence pattern of a normal artery. This has been indicated to suggest that a laser may be controlled as a function of fluorescence to ablate only atherosclerotic tissue. However, known efforts to apply this theory in practice have so far been unsuccessful, one reason being the tendency of the laser to char the tissue thereby obscuring the fluorescence pattern.

OBJECTS OF THE INVENTION

The main object of this invention is to provide an improved laser ablation process and apparatus.

More specifically, it is an object of this invention to provide a fluorescence controlled laser ablation process and apparatus wherein the ablated tissue is not charred.

It is a further object of the invention to provide a laser angioplasty system in which the likelihood of damage to normal arterial tissue is greatly reduced.

SUMMARY OF THE INVENTION

In accordance with the invention, high power ultraviolet laser energy is directed at an area to be ablated by means of an optical fiber. A low power laser is used to cause the tissue at which the high power laser is directed to fluoresce. The fluorescence pattern is analyzed, for example, in a computer and the high power laser controlled depending on the detected fluorescence pattern so that only atherosclerotic (or cancerous) tissue is ablated. Selected ultraviolet frequencies are used for ablation so that charring of the tissues does not occur. When the abnormal tissue has been ablated, actuation of the high power laser is inhibited.

IN THE DRAWINGS

DETAILED DESCRIPTION

A laser ablation system in accordance with the invention can be used for the removal of atherosclerotic plaque and cancerous tissues. In its currently preferred embodiment, the invention is intended to be used for the abltion of atherosclerotic plaque; accordingly, the description of the preferred embodiment is directed to laser angioplasty.

Figure 1:
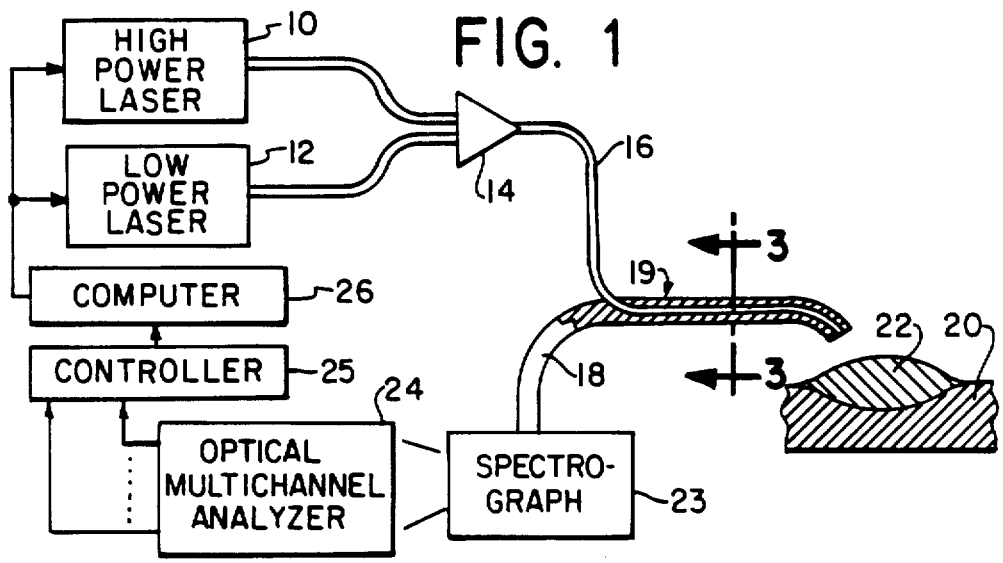
FIG. 1 is a block diagram of a laser ablation system in accordance with the invention.
Figure 3:
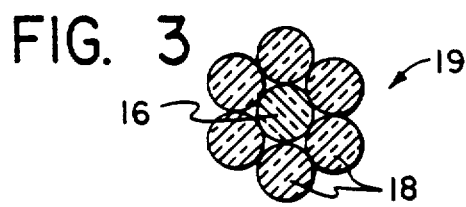
FIG. 3 is a cross-section of preferred fiberoptic catheter which may be employed in accordance with the invention.

The components of the invention are shown in FIG. 1. A high power laser 10 provides the energy to ablate the atherosclerotic plaque. A low power laser 12 is used to cause the plaque to fluoresce. As explained below, it is contemplated that a single laser may provide the functions of the two lasers 10 and 12. The outputs of lasers 10 and 12 are coupled through a fiberoptic coupler 14 to an optical fiber 16. In a preferred embodiment, fiber 16 is enveloped by a bundle of fibers 18 to form a coaxial fiberoptic catheter 19 which may be inserted into the artery of a patient. A cross-section of the catheter 19 is shown in FIG. 3. The fiber 16 and each of the fibers 18 comprises a conventional core enveloped by a cladding material to minimize the loss of optical energy within the fiber. The fiber bundle 18 and fiber 16 could be replaced by a single fiber and beam splitter as explained below.

An arterial wall is shown diagrammatically at 20 with atherosclerotic plaque at 22. The catheter 19 is inserted into the artery and positioned until it is directed at the plaque 22. Proper positioning, as will become apparent from the following description, is determined by the fluorescence pattern of the tissue. As the catheter is positioned within the artery, the low power laser 12 illuminates the tissue to produce fluorescence which is detected by the fiber bundle 18 and returned to a spectograph 23 which disperses the light according to wavelength and images the optical spectrum onto an optical multi-channel analyzer 24. The analyzer 24 produces a multi-channel electrical output that represents the fluorescence spectrum in analog form. These analog signals (each corresponding to a portion of the spectrum) are converted to a corresponding multiplicity of serial digital signals by a controller 25 and fed to a computer 26. The computer is programmed to generate a control signal that causes the high power laser 10 to fire when the distal end of catheter 19 is aimed at plaque 22. After completion of plaque ablation, the fluorescence pattern changes from "atherosclerotic" to "normal" and inhibits further firing of the high power laser 10. A similar operation will be used for cancerous tissue ablation where 22 represents the tumor, and 20 the underlying normal tissue.

The optical multi-channel analyzer 24 may comprise a linear diode array (for example, Princeton Applied Research Model No. 1420) including 1,024 photocells coupled to a micro-channel plate intensifier. Less than all of the photocells may be used for a particular application. The parallel photocell signals are coupled to the controller 25 (Princeton Applied Research Model 1218) which interfaces with the computer 26. Standard techniques may be used to improve signal-to-noise ratio and to correct for background fluorescence or other extraneous signals. For example, the endogenous fluorescence of blood may be subtracted from the tissue fluorescence spectrum to minimize the possibility that the fluorescence will obscure valuable tissue fluorescence patterns. Calibration for wavelength and intensity may be accomplished by comparison with frequency spectra obtained from mercury and neon vapor lamps, and an NBS traceable calibrated tungsten halogen lamp A principal feature of the invention is the ability to ablate the atherosclerotic plaque 22 in such a way as to avoid charring. If charring occurs, the fluorescence pattern is obscured and the system may therefore be unable to distinguish between atherosclerotic and normal arterial tissue. The laser ablation system of the invention avoids this serious drawback by a combination of features including the frequency of the laser and the construction of the catheter which ensures that the high power laser energy is directed precisely at the tissue which is undergoing fluorometric analysis. Moreover, because the invention is capable of recognizing different types of plaque or cancerous tissue, a greater degree of reliability is possible in accordance with the invention.

Recognition of Plaque

Examination of human aorta indicates that tissue may be classified grossly and histologically as normal, thin yellow fatty plaque, and thick white atheromatous plaque. These different types of plaque produce different fluorescence patterns and it may be necessary to identify not only the presence of, but also the type of plaque. The patterns will differ also depending on the wavelength of the illuminating source. Ultraviolet frequencies are preferred because they stimulate more fluorescence than higher frequencies which means that more information is contained in the patterns. As one example, the fluorescence induced by a pulsed nitrogen laser (Lambda Physik Model M-100A) at a wavelength of 337 nm (2.5 mj pulses at a pulse rate of 10 hz) produces the fluorescence spectra shown in FIG. 2, curve 30 representing the fluorescence pattern for normal arterial wall, curve 32 the pattern for yellow plaque, and curve 34 the pattern for white plaque. By comparing the fluorescence intensities at selected wavelengths (e.g., 448 nm, 514 nm, and 538 nm) it is possible to identify reliably both types of plaque.

More precise discrimination between normal and atherosclerotic tissue is possible using computer aided regression analysis of the fluorescence spectra. For example, a laser induced fluorescence (LIF) score can be derived by stepwise multivariate regression analysis to distinguish the normal and atherosclerotic tissues based on the fluorescence intensities of selected wavelengths (e.g., 398, 447, 452, 484, 493 and 510 nm). Using a helium-cadmium laser (Omnichrome Model 356-5MS; 10 mw continuous wave power at a wavelength of 325 nm, beam diameter 0.9 mm) an LIF score for normal tissue was 1.01 plus or minus 0.11. The LIF score for atherosclerotic tissue was 1.94 plus or minus 0.14 (p less than 0.001).

There are known ways to recognize the patterns which typify plaque (for example, computer aided) and the invention contemplates the use of any technique which enables reliable discrimination between the normal and atherosclerotic tissues.

The High Power Laser

Charring is dependent upon the wavelength and peak power density of the high power laser 10. Peak power density may be defined as peak power per unit area, where peak power is equal to the pulse energy divided by pulse duration. At any frequency, charring will not occur if peak power density exceeds a threshold which is inversely proportional to the absorption of laser energy by the tissue. Tissue absorption in turn is dependent on wavelength. Thus, increasing wavelength from the ultraviolet through the visible range (decreasing frequency) decreases tissue absorption which raises the threshold. It is necessary that there be a balance between the peak power density and frequency to achieve the desired result since if peak power density is too high, it is difficult, if not impossible, to conduct the laser energy through an optical fiber. While it is possible to use both ultraviolet and mid-infrared frequencies, wavelengths between about 280 and 400 nm are preferred because, at these frequencies, silicon fibers can conveniently be used to conduct the optical energy through the catheter.

Ideally, all of the laser energy should be used to vaporize the plaque. To the extent the energy is not absorbed by atherosclerotic tissue, it tends to heat the surrounding tissue, thereby increasing the likelihood of thermal damage. As pulse energy per unit area increases, the time required for ablation (and, therefore, the likelihood of thermal damage) decreases.

Currently, based on observations and theoretical conclusions, it is believed that ablation without charring is possible using a pulsed laser at a wavelength between 280 nm and 400 nm with a pulse duration of 100–500 ns wherein the pulse energy per unit area is greater than 20 $mJ/mm^2$. Good results have been obtained experimentally using a frequency-doubled, Q-switched Alexandrite laser (wavelength 378 nm, pulse duration 60 ns, repetition rate 28 Hz with pulse energy per unit area in the range of 50–96 $mJ/mm^2$). There was a marked decrease in the time required for ablation (and in the occurence of charring) when the pulse energy per unit area was greater than 35 $mJ/mm^2$. Satisfactory experimental results have also been obtained with an excimer laser (308 or 351 nm) and a flashlight pumped dye laser (450 nm).

It is contemplated that a single laser may serve the functions of lasers 10 and 12. This would require that the single laser be switchable between high and low power outputs to alternately fluoresce and ablate.

The Fiberoptics

The key factors in the fiberoptical system are (1) that the high power fiber 16 and the fluorescent sensing fibers 18 be directed at the same tissue; and (2) that the laser energy be coupled to the fiber 16 without causing excessive heat buildup. The coaxial arrangement of the fiber bundle 18 with the fiber 16 (FIG. 3) is advantageous as compared to other conventional fiber arrangements (e.g., hemispherical or random) since it is relatively easy to ensure that the outer fibers 18 are focused at the same point as the high power fiber 16. It is also possible to use a single fiber for both the high power and lower power energy with suitable multiplexing devices (not shown) to direct the reflected fluorescent energy to the optical multi-channel analyzer. Using a wet silica fiber, a peak in the reflected light intensity was found to occur when the end of catheter 19 is about 0.020 inches from the target. Pure "wet" silica fibers are preferred because they provide low loss at ultraviolet frequencies. One such "wet" silica is sold under the trademark SUPERSIL II by Heraeus-Amersil, Inc. of Sayreville, N.J.

The fiberoptic coupler 14 must be capable of coupling the high and low power laser energy into the fiber 16 without heat buildup. This requires precise alignment and a high precision connector of the type, for example, used for telecommunications. The fibers may be coated with a polymeric material chosen for mechanical durability and heat resistant characteristics. These coatings must also be free from attack by blood or other environmental fluids which they are likely to encounter and biocompatible with the environment. The catheter which houses the fiber optics may also include channels for the purpose of introducing a saline flush or guide wire to the area undergoing preparation.

For purposes of intravascular irradiation, a relatively small diameter optical fiber is required to minimize the size of the catheter and also to increase flexibility. This increases power density at the fiber input which may require decreased pulse energy and a corresponding increase in pulse repetition rate to maintain constant average power, or an increase in pulse duration. Self focusing fiberoptic lenses, sapphire ball lenses, or spherical curvatures mechanically polished on the fibers may be used to reduce heating of the fibers.

Operation

The system may be arranged to ablate only when atherosclerotic tissue is encountered or, alternatively, ablation may be inhibited only when normal arterial tissue is detected. For example, when the fluorescence induced by the low power laser 12 indicates that the catheter 19 is directed at atherosclerotic plaque, a series of high power ablative pulses may be triggered from the high power laser 10. Following the series of pulses, a further fluorometric analysis may be used to assess for the residual presence of atherosclerotic plaque. A further series of high power ablative pulses may be triggered until a fluorescence spectrum indicative of normal arterial tissue is detected, at which point the catheter can be redirected (manually or automatically) until additional atherosclerotic tissue is detected. The alternative would be to continuously transmit high power ablative pulses which would be inhibited when normal arterial wall is sensed.

What is claimed is:

1. Apparatus for ablating atherosclerotic tissue in blood vessels, comprising:
   a source of low power ultraviolet laser energy having a wavelength outside the band of visible wavelengths,
   fiberoptic means for directing said low power laser energy at a section of tissue of said blood vessel to cause said section to fluoresce,
   spectrum analyzing means for determining whether a laser induced fluorescence frequency spectrum is representative of normal or atherosclerotic tissue,
   a source of high power laser energy for producing pluses, the pulse duration and energy per unit area of which are selected to cause ablation without charring of tissue that would obscure the fluorescence pattern of the tissue,
   fiber optic means for directing the output of said high power ultraviolet laser at said section of tissue, and
   means responsive to said spectrum analyzing means for enabling atherosclerotic tissue to be progressively ablated by said high power laser energy while said tissue is caused to fluoresce by said low power ultraviolet laser until said spectrum analyzing means indicates that the fluorescence pattern of said tissue is no longer indicative of atherosclerotic tissue thereby to ablate said atherosclerotic tissue only.

2. Apparatus according to claim 1, wherein said source of high power laser energy comprises a pulsed laser, the output of which has a wavelength between 280 nm and 400 nm, a pluse duration between 10 and 500 ns and wherein the pulse energy per unit area is greater than 20 mJ/mm$^2$.

3. Apparatus according to claims 1 or 2, wherein said two fiber optic means comprise a central fiber for said high power source and a plurality of optical fibers for said low power source enveloping said central fiber.

4. Apparatus according to claims 1 or 2, wherein said two fiberoptic means comprise a single fiber.

5. Apparatus according to claim 2, wherein the pulse energy per unit area of the pulses produced by said high power laser is greater than 35 mJ/mm$^2$ and the frequency of the laser is in the near ultraviolet range.

6. A method for ablating atherosclerotic plaque, comprising:
   directing a low power ultraviolet laser having a wavelength outside the band of visible wavelengths at a selected section of a blood vessel to cause fluorescence of the tissue in said section,
   analyzing the frequency spectrum of such fluorescence to determine whether the section of the blood vessel at which said low power laser is directed is normal or atherosclerotic,
   providing a high power laser having an output in the form of pulses, the pulse duration and pulse energy per unit area of said pulses being selected so as to cause ablation without charring,
   directing the pulses from said high power laser at said section if said step of analyzing the frequency spectrum indicates that said section is atherosclerotic,
   continuing to irradiate the tissue with said low power ultraviolet laser energy to cause said tissue to fluoresce,
   analyzing the fluorescence spectrum as the tissue is caused to fluoresce, and
   discontinuing the laser ablation process when the fluorescence pattern of the tissue indicates that it is no longer atherosclerotic.

7. A method according to claim 6, wherein the step of providing a high power laser comprises providing a laser having an output in the form of pulses having a pulse energy per unit area greater than 35 mJ/mm$^2$.

8. A method according to claim 6, wherein the step of providing a high power laser comprises providing a laser having an output in the form of pulses having a wavelength between 280 nm and 400 nm and a pulse duration between 10 ns and 500 ns, the pulse energy per unit area being greater than 20 mJ/mm$^2$.

9. A method according to claim 8 wherein the pulse energy per unit area is greater than 35 mJ/mm$^2$.

* * * * *

UNITED STATES PATENT AND TRADEMARK OFFICE
CERTIFICATE OF CORRECTION

PATENT NO. : 4,785,806

DATED : November 22, 1988

INVENTOR(S) : Lawrence I. Deckelbaum

Page 1 of 3

Figure 2:
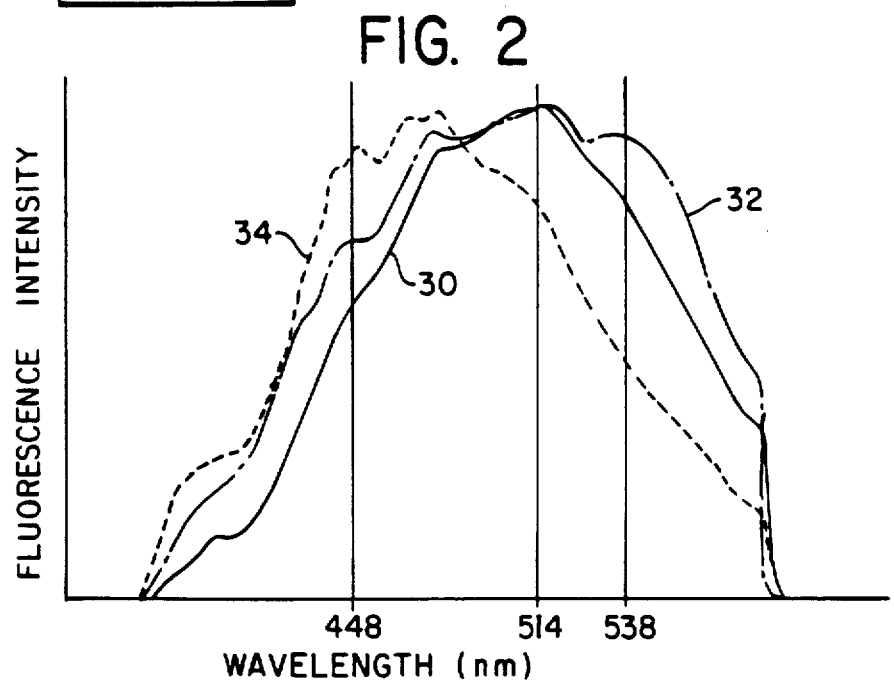
FIG. 2 is a series of curves of fluorescence intensity versus wavelength showing typical fluorescence patterns for normal arterial tissue and atherosclerotic tissue.

It is certified that error appears in the above-identified patent and that said Letters Patent is hereby corrected as shown below:

The Title Page and Figures 1-3 should be deleted to appear as per attached sheets.

Signed and Sealed this

Eighteenth Day of April, 1989

Attest:

DONALD J. QUIGG

*Attesting Officer*

*Commissioner of Patents and Trademarks*

United States Patent [19]

Deckelbaum

[11] Patent Number: 4,785,806
[45] Date of Patent: Nov. 22, 1988

[54] LASER ABLATION PROCESS AND APPARATUS

[75] Inventor: Lawrence I. Deckelbaum, Woodbridge, Conn.

[73] Assignee: Yale University, New Haven, Conn.

[21] Appl. No.: 1,376

[22] Filed: Jan. 8, 1987

[51] Int. Cl.⁴ .............................................. A61N 5/06
[52] U.S. Cl. ................................... 128/303.1; 128/634; 128/666
[58] Field of Search ............... 128/303.1, 395, 634, 128/653, 665–667; 219/121 L, 121 LA, 121 LB, 121 LM; 604/20

[56] References Cited

U.S. PATENT DOCUMENTS

| | | | |
|---|---|---|---|
| 4,556,057 | 12/1985 | Hiruma et al. | 128/395 |
| 4,641,650 | 2/1987 | Mok | 128/303.1 |
| 4,641,912 | 2/1987 | Goldenberg | 128/303.1 |
| 4,648,892 | 3/1987 | Kittrell | 128/303.1 |
| 4,681,104 | 7/1987 | Edelman | 128/303.1 |
| 4,686,979 | 8/1987 | Gruen et al. | 128/303.1 |

FOREIGN PATENT DOCUMENTS

| | | | |
|---|---|---|---|
| 111060 | 6/1984 | European Pat. Off. | 128/303.1 |
| 8606642 | 11/1986 | PCT Int'l Appl. | 128/303.1 |

OTHER PUBLICATIONS

"Use of Pulsed Energy Delivery . . . " by Deckelbaum et al.; J. Am. Coll. Cardiol., No. 4, 1986, pp. 848–908.
"Reduction of Laser Induced . . . " by Deckelbaum et al.; Am. J. Cardiol., vol. 56, 10/1/85, pp. 662–666.
"For Ultraviolet Laser Ablation of Atherosclerotic Lesions" by Linsker et al., Lasers in Surg. & Med., 4/1984; pp. 201-206.
"Selective Absorption of Ultraviolet Laser Energy . . . " by Murphy–Chutorian Am. J. Cardiol., vol. 5; 5/85; pp. 1293–1297.
"Detection of Aortic Atheromatrosis . . . " by Edholm et al.; J. of Atherosclerosis Res., vol. 5; 1965; pp. 592–595.

Primary Examiner—Lee S. Cohen
Assistant Examiner—David Shay
Attorney, Agent, or Firm—Darby & Darby

[57] ABSTRACT

A process and apparatus for ablating atherosclerotic or tumorous tissues is disclosed. Optical fibers direct low power light energy at a section of tissue to be ablated to cause the section to fluoresce. The fluorescence pattern is analyzed to determine whether the fluorescence frequency spectrum is representative of normal or abnormal tissue. A source of high power ultraviolet laser energy directed through an optical fiber at the section of tissue is fired only when the fluorometric analysis indicates that it is directed at abnormal tissue.

9 Claims, 2 Drawing Sheets

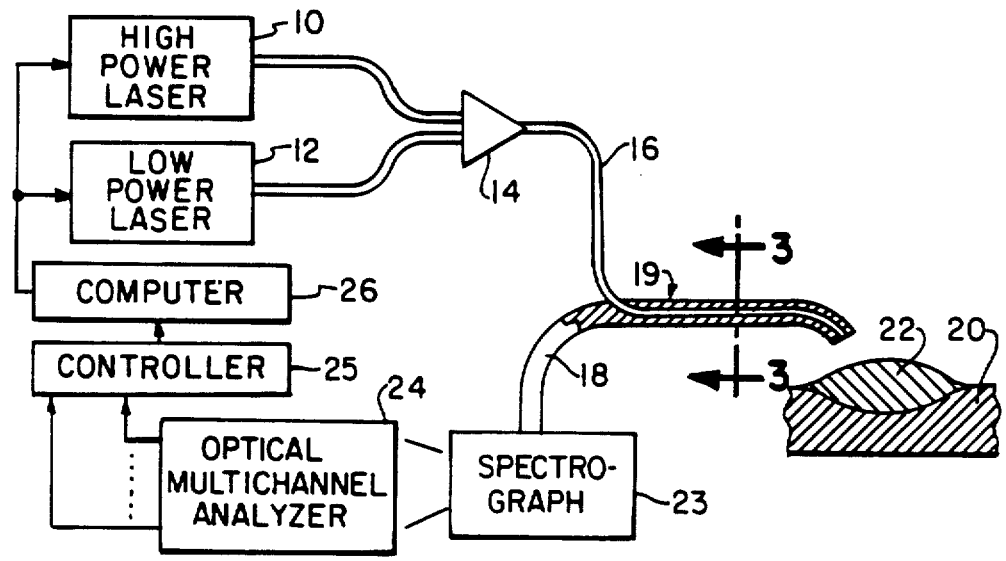

UNITED STATES PATENT AND TRADEMARK OFFICE
CERTIFICATE OF CORRECTION

PATENT NO. : 4,785,806
DATED : November 22, 1988
INVENTOR(S) : Lawrence I. Deckelbaum It is certified that error appears in the above-identified patent and that said Letters Patent is hereby corrected as shown below:

Col. 5, line 44, change "pluses" to --pulses--;

Col. 5, line 48, after "said" insert --source of--;

Col. 5, line 49, delete "ultraviolet"; after "laser" insert --energy--.

Signed and Sealed this

Ninth Day of January, 1990

Attest:

JEFFREY M. SAMUELS

Attesting Officer     Acting Commissioner of Patents and Trademarks